United States Patent [19]
Hiraga et al.

[11] 4,226,616
[45] Oct. 7, 1980

[54] DIPHENYL ETHER AND HERBICIDE CONTAINING THE SAME

[75] Inventors: Kunikazu Hiraga, Izumi; Shoichi Shibayama, Takatsuki; Isao Yanai, Osaka; Tatsuo Harada, Kawachinagano, all of Japan

[73] Assignee: Nihon Nohyaku Co., Ltd., Tokyo, Japan

[21] Appl. No.: 872,338

[22] Filed: Jan. 25, 1978

[30] Foreign Application Priority Data

Jan. 31, 1977 [JP] Japan .................................. 52-9463

[51] Int. Cl.² ...................... C07C 41/00; C07C 43/22; A01N 9/24
[52] U.S. Cl. ........................................ 71/124; 568/586
[58] Field of Search ...................... 260/613 R; 71/124; 568/586

[56] References Cited

U.S. PATENT DOCUMENTS 3,265,741  8/1966  Sheppard .......................... 260/613 R

FOREIGN PATENT DOCUMENTS 38-9898 6/1963 Japan.
45-27116 9/1970 Japan.

Primary Examiner—Bernard Helfin
Attorney, Agent, or Firm—Cushman, Darby & Cushman

[57] ABSTRACT

A diphenyl ether represented by the general formula (I),

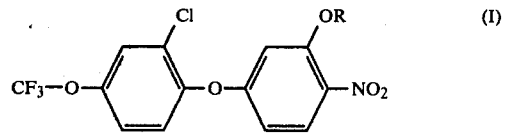

wherein R is a lower alkyl group having 1 to 4 carbon atoms, a lower alkoxyethyl group, the alkoxy substituent of which having 1 to 4 carbon atoms, or a lower alkoxyethoxyethyl group, the alkoxy substituent of which having 1 to 4 carbon atoms is capable of controlling annual and perennial weeds.

14 Claims, No Drawings

DIPHENYL ETHER AND HERBICIDE CONTAINING THE SAME

This invention relates to diphenyl ethers represented by the general formula (I),

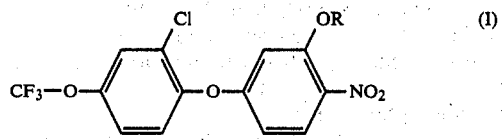

wherein R is a lower alkyl group having 1 to 4 carbon atoms, a lower alkoxyethyl group, the alkoxy substituent of which having 1 to 4 carbon atoms, or a lower alkoxyethoxyethyl group, the alkoxy substituent of which having 1 to 4 carbon atoms. It relates further to a process for producing said ether and the usage of said ether.

The compound represented by the general formula (I) is useful especially as a herbicide (including an algicide; the same applies hereinafter).

The compound represented by the general formula (I) is a novel compound not found in the literature. It is readily synthesized, for example, by a synthetic route shown schematically below,

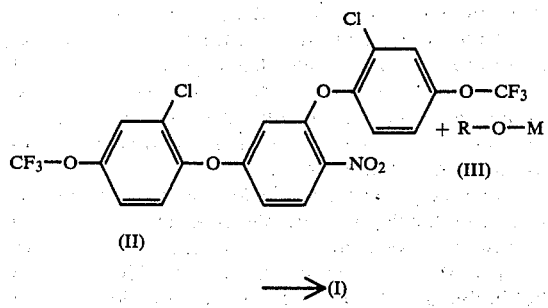

wherein R is the same as defined above and M is an alcoholate-forming metal atom. Thus, the intended compound can be readily synthesized in a high yield by allowing 2,4-bis(2-chloro-4-trifluoromethoxyphenoxy)-nitrobenzene and an alcoholate to react in a suitable inert solvent. Suitable solvents are hydrocarbons such as, for example, benzene and toluene, though other solvents which will not interfere with progress of the reaction can also be used. The mole ratio of the nitrobenzene derivative of the formula (II) to the alcoholate of the formula (III) is 1:10 to 1:1, preferably 1:2 to 1:1.2. The reaction can be carried out at a temperature, for example, in the range of 20° to 120° C. After completion of the reaction, the intended reaction product is separated in a customary way, for example, by washing the reaction mixture with water and evaporating the solvent in vacuum and, if necessary, further purified, for example, by silicagel chromatography. Among the product thus obtained, those represented by the formula (I) wherein R is methyl, ethyl, methoxyethyl, ethoxyethyl, methoxyethoxyethyl or ethoxyethoxyethyl are preferable. Typical examples of the compounds are as shown below.

| Compound No. | R in general formula (I) | Melting point or refractive index |
|---|---|---|
| 1 | $CH_3$ | $n_D^{20}$ 1.5562 |
| 2 | $C_2H_5$ | m.p. 69–71° C. |
| 3 | $CH_3OCH_2CH_2$ | $n_D^{20}$ 1.5442 |
| 4 | $C_2H_5OCH_2CH_2$ | $n_D^{20}$ 1.5330 |
| 5 | $CH_3OCH_2CH_2OCH_2CH_2$ | $n_D^{20}$ 1.5179 |
| 6 | $C_2H_5OCH_2CH_2OCH_2CH_2$ | $n_D^{20}$ 1.5206 |

The above-noted diphenyl ethers are capable of controlling annual and perennial weeds grown in paddy field, upland field, orchard and swamp, such as barnyard grass (*Echinochloa Crusgalli* L., an annual gramineous grass which is a typical strongly injurious weed grown in paddy field), monochoria (*monochoria vaginalis* Presl., a strongly injurious annual weed of Pontederiaceae family grown in paddy field), umbrella plant (*Cyperus difformis* L., an injurious annual cyperaceous weed grown in paddy field), slender spikerush (*Eleocharis acicularis* Roem. et Schult, a typical injurious perennial weed of a paddy field, grown also in swamp and waterway), Arrowhead (*Sagittaria pygmaea* Miq., an injurious perennial weed of Alismataceae family, grown in paddy field, swamp and ditch), Hotarui (*Scirpus juncoides* Roxb. Var. Hotarui ohwi. a perennial cyperaceous weed grown in paddy field, swamp and ditch), large crabgrass (*Digitaria adschendeus* Henr., an annual gramineous grass which is a typical strongly injurious weed grown in upland field and orchard) and Redroot pigweed (*Amaranthus varidis* L., an annual weed of Amaranthus family grown in vacant land, roadside and upland field).

A current trend in paddy rice cultivation is a rapid spread of mechanical transplanting of young rice seedlings which have low chemical resistance. Consequently, development of an early stage herbicide having a selectivity higher than those of conventional herbicides is strongly demanded. Because of their highly selective herbicidal activities, the compounds represented by the general formula (I) become most valuable herbicides in paddy rice cultivation by use of the above-said technique of young seedling transplantation and a technique of direct sowing of paddy rice on well-drained paddy field, both techniques requiring a highly selective herbicide.

Since the compounds of the general formula (I) exhibit an excellent controlling action against weeds in the initial stage of growth, their characteristic physiological activities can be manifested effectively by treating with the compounds the areas in which useful plants are to be grown or the areas in which useful plants have already been planted (including such areas as orchard where the useful plants have been set out) but weeds have not yet emerged or by treating the areas in which useful plants have been sown but not yet emerged. The modes of the use of the present herbicide compound are not limited to those described above. It can be used as a middle stage herbicide in paddy fields and, further, as a herbicide for controlling such general weeds as those usually grown on, for example, reaped fields, temporarily non-cultivated paddy fields and upland fields, ridges between paddy fields, agricultural pathways, waterways, prepared lands intended for use as pasture, graveyards, parks, roads, playgrounds, unoccupied areas of the building sites, reclaimed lands, railways, and forests. Herbicidal treatment of such areas is carried out preferably (and also economically) but not necessarily prior to the emergence of weeds.

In using the present compound as a herbicide, it is employed generally in a form which is convenient for use and prepared by following the customary pesticide formulating procedures. Thus, the present compounds may be blended with suitable inert carriers and, if necessary, auxiliary agents to effect dissolution, dispersion, simple mixing, impregnation, adsorption, or adhesion, resulting in dispersions, emulsifiable concentrates, solutions, wettable powders, dusts, granules, tablets, etc.

The inert carriers to be used in the formulations may be either solids or liquids. Examples of the materials usable as solid carriers include vegetable powders such as soybean flour, cereal flour, wood flour, bark flour, saw dust, powdered tobaco stalk, powdered walnut shell, bran, powdered cellulose, and extraction residues of vegetables; cellulosic materials such as paper, corrugated fiberboards, and rags; synthetic polymers such as powdered synthetic resins; inorganic and mineral products such as clays (for example, kaolin, bentonite and acid clay), talcs (for example, talc and pyrophyllite), siliceous substances [for example, diatomaceous earth, siliceous sand, mica, and "white carbon" (commercial highly dispersed synthetic silicic acid, also called hydrated finely divided silicon or hydrated silicic acid; some products contain calcium silicate as major ingredient)], activated carbon, powdered sulfur, pumice, calcined diatomaceous earth, disintegrated brick, fly ash, sand, calcium carbonate and calcium phosphate; chemical fertilizers such as ammonium sulfate, ammonium phosphate, ammonium nitrate, urea and ammonium chloride; and farmyard manure. These materials are used each alone or as mixtures of two or more of these.

The materials usable as liquid carriers are selected from those which are solvents for the active compounds and those which are non-solvents but can disperse the active compounds by the aid of auxiliary agents. Examples of liquid carriers which are used each alone or in combinations of two or more are as follows: water, alcohols (for example, methanol, ethanol, isopropanol, butanol and ethylene glycol), ketones (for example, acetone, methyl ethyl ketone, methyl isobutyl ketone, diisobutyl ketone and cyclohexanone), ethers (for example, ethyl ether, dioxane, Cellosolves, dipropyl ether and tetrahydrofuran), aliphatic hydrocarbons (for example, gasoline and mineral oils), aromatic hydrocarbons (for example, benzene, toluene, xylene, solvent naphtha and alkylnaphthalenes), halohydrocarbons (for example, dichloroethane, chlorinated benzenes, chloroform and carbon tetrachloride), esters (for example, ethyl acetate, dibutyl phthalate, diisopropyl phthalate and dioctyl phthalate), acid amides (for example, dimethylformamide, diethylformamide and dimethylacetamide), nitriles (for example, acetonitrile) and dimethyl sulfoxide.

The auxiliary agents which are used are as shown below. These substances are used in accordance with the purpose. In some cases, combinations of two or more auxiliary agents are used. In some other cases, no auxiliary agent is used at all.

For the purpose of emulsification, dispersion solubilization or wetting of the active compounds, surface active agents are used. Examples of such agents are polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of stabilization of dispersions, tackification or agglomeration of the active compound, it is possible to use, for example, casein, gelatin, starch, aliginic acid, methylcellulose, carboxymethylcellulose, gum arabic, polyvinyl alcohol, turpentine oil, rice bran oil, bentonite and ligninsulfonates.

For the purpose of improving the flow property of solid compositions, it is possible to use waxes, stearates and alkyl phosphates.

As peptizers for a dispersible composition, it is possible to use naphthalenesulfonic acid condensation products and polyphosphates.

It is also possible to add a defoamer such as, for example, silicone oils.

The proportion of the active compound in the formulation can be varied as required. A suitable proportion of the active compound is usually 0.5 to 20% by weight in a dust or granule and 0.1 to 50% by weight in an emulsifiable concentrate or wettable powder.

For destroying various weeds or inhibiting their growth or protecting useful plants from the injury due to weeds, a weed destroying dosage or a weed growth inhibiting dosage of the present herbicidal composition is applied as such or after suitable dilution with water and the like or in the form of dispersion to the soil or the foliage of weeds in the area where the emergence or growth of weeds is undesirable.

The amount to be used of the present herbicide depends on various factors such as, for example, purpose, weeds to be controlled, state of emergence or growth of weeds or crops, tendency of the emergence of weeds, weather, environmental conditions, type of the herbicide composition, mode of application, areas to be applied, and time of application.

In using the present herbicidal composition alone as a selective herbicide, it is suitable to select the dosage of the present active compound from the range of 45 to 250 g per 10 ares. When it is used in combination with other herbicides, it is possible to select the dosage from the range of smaller rates of application by taking into account the increased efficacy of the combined use as compared with the single use.

The present herbicide is especially valuable for the pre-emergence treatment of upland fields and for the early stage or middle stage control of weeds in paddy fields. The present invention embraces also the combined use with other herbicides in order to enlarge the range of controllable weed species or the range of time in which weeds are effectively controlled or to reduce the dosage of the present compound. For each purposes mention may be made of the combined use with, for example, one or more of phenoxy fatty acid herbicides such as, for example, 2,4-PA's (for example, ethyl 2,4-dichlorophenoxyacetate), MCP's (for example, ethyl 2-methyl-4-chlorophenoxyacetate, sodium 2-methyl-4-chlorophenoxyacetate and allyl 2-methyl-4-chlorophenoxyacetate) and MCPB (ethyl 2-methyl-4-chlorophenoxybutyrate); diphenyl ether herbicides such as, for example, NIP (2,4-dichlorophenyl 4'-nitrophenyl ether), CNP (2,4,6-trichlorophenyl 4'-nitrophenyl ether) and chlomethoxynil (2,4-dichlorophenyl 3'-methoxy-4'-nitrophenyl ether); s-triazine herbicides such as, for example, CAT [2-chloro-4,6-bis(ethylamino)-s-triazine], Prometryne [2-methylthio-4,6-bis(isopropylamino)-s-triazine] and Simetryne [2-methylthio-4,6-bis(ethylamino)-s-triazine]; carbamate herbicides such as, for example, molinate (S-ethylhexahydro-1H-azepine-1-carbothioate), MCC [methyl N-(3,4-dichlorophenyl)-carbamate], IPC [isopropyl N-(3-chlorophenyl)-carbamate] and Benthiocarb [S-(4-chlorobenzyl) N, N-diethylthiocarbamate]; and others such as DCPA (3,4-dichloropropionanilide), Butachlor [2-chloro-2',6'-diethyl-N-(butoxymethyl)acetanilide, alachlor [2-chloro-2',6'-diethyl-N-(methoxymethyl)acetanilide, and bentazon [3-isopropyl-2,1,3-benzothiadiazinone-(4)-2,2-dioxide]. The above abbreviations conform to the description in "Pesticide Manual, 1976" published by Japan Plant Protection Association.

The following examples illustrate this invention but are not intended to limit it in any way.

EXAMPLE 1

Synthesis of 3-methoxy-4-nitro-2'-chloro-4'-trifuoromethoxy(diphenyl ether) (Compound No. 1)

A solution of 0.1 g of metallic sodium in 8 ml of methanol was added to a solution of 1.2 g (0.002 mole) of 2,4-bis(2-chloro-4-trifluoromethoxy-phenoxy)nitrobenzene in benzene. The mixture was heated with stirring at 40°–50° C. in a water bath for 1.5 hours. The reaction mixture was thoroughly washed with a dilute aqueous sodium hydroxide solution and then with water, dehydrated over anhydrous sodium sulfate, and freed from the benzene by distillation to obtain a crude product. The crude product was purified by chromatography on silica gel to obtain 0.7 g of the intended product ($n_D^{20}$ 1.5562; 84% yield). 2,4-Bis(2-chloro-4-trifluoromethoxyphenoxy)-nitrobenzene was synthesized in the following way: 11.0 Grams (0.044 mole) of potassium 2-chloro-4-trifluoromethoxyphenolate and 3.2 g (0.017 mole) of 2,4-dichloronitrobenzene were heated under reflux in 100 ml of dimethylformamide for one hour. After cooling, the reaction mixture was poured into about 500 ml of water and then extracted with benzene. The benzene layer was thoroughly washed successively with dilute aqueous sodium hydroxide solution, dilute hydrochloric acid and water, then dehydrated, and concentrated. The resulting oily substance was distilled under reduced pressure to obtain 5.3 g (57% yield) of the intended product boiling at 170°–185° C./0.1 mmHg.

EXAMPLE 2

Synthesis of 3-methoxyethoxyethoxy-4-nitro-2'-chloro-4'-trifluoromethoxy(diphenyl ether) (Compound No. 5)

A solution of 0.1 g of metallic sodium in 10 ml of methyl Carbitol was added to about 100 ml of a benzene solution containing 1.2 g (0.002 mole) of 2,4-bis(2-chloro-4-trifluoromethoxyphenoxy)nitrobenzene. The mixture was stirred for 2 hours while being heated at 50°–60° C. in a water bath. The reaction mixture was thoroughly washed successively with a dilute aqueous solution of sodium hydroxide and water, then dehydrated over anhydrous sodium sulfate, and freed from the benzene by distillation to obtain a crude product. The crude product was purified by chromatography on silica gel to obtain 0.8 g of the intended product ($n_D^{20}$ 1.5179; 80% yield).

EXAMPLE 3

Synthesis of 3-methoxyethoxy-4-nitro-2'-chloro-4'-trifluorometoxy(diphenyl ether) (Compound No. 3).

A solution of 0.1 g of metallic sodium in 10 ml of methyl Cellosolve was added to a solution of 1.2 g of 2,4-bis(2-chloro-4-trifluoromethoxyphenoxy)nitrobenzene in benzene. The mixture was treated as in Example 1 to obtain 0.8 g of the intended product ($n_D^{20}$ 1.5442; 85% yield).

In the following Examples all parts are by weight.

EXAMPLE 4

| | Parts |
|---|---|
| Compound No. 1 | 50 |
| Clay-white carbon mixture containing major proportion of clay | 45 |
| Polyoxyethylene nonylphenyl ether | 5 |

The above ingredients were uniformly mixed and ground to prepare a wettable powder.

EXAMPLE 5

| | Parts |
|---|---|
| Compound No. 3 | 5 |
| Bentonite-clay mixture | 90 |
| Calcium ligninsulfonate | 5 |

The above ingredients were uniformly mixed and ground. The mixture was kneaded together with a suitable amount of water and granulated to obtain a granule preparation.

EXAMPLE 6

An emulsifiable concentrate was prepared by mixing together the following ingredients:

| | Parts |
|---|---|
| Compound No. 1 | 50 |
| Xylene | 40 |
| Mixture of polyoxyethylene nonylphenyl ether and calcium alkylbenzene sulfonate | 10 |

TEST EXAMPLE 1

A number of 1/10,000-are pots were filled with soil to simulate a paddy field and grown with injurious weeds of the leaf ages (plant ages in leaf number) shown below. Besides, on the day before the chemical treatment, young rice seedlings of the 2.5 leaf stage were transplanted into the pot. The pots were subjected to chemical treatment (the chemical used was the emulsifiable concentrate of Example 6 extended with water). After 21 days, the percent control of growth was estimated by reference to untreated plot. The results obtained were as shown in Table 1.

| Weed species under test and their leaf stage | |
|---|---|
| | Leaf stage |
| Barnyard grass | 1 |
| Monochoria | 2–3 |
| Umbrella plant | 2–3 |
| Slender spikerush | Early stage of |

| Arrowhead | multiplication 3 |
|---|---|
| Evaluation | |
| (1) Herbicidal activity | Percent growth control relative to untreated plot |
| 5 | 100% |
| 4 | 90–99 |
| 3 | 80–89 |
| 2 | 60–79 |
| 1 | <60 |
| (2) Chemical injury | |
| H | High (including withering) |
| M | Medium |
| L | Low |
| N | None |

TABLE 1

| Compound No. | Dosage of active ingredient (g/are) | Rice | Barnyard grass | Monochoria | Umbrella plant | Slender spikerush | Arrowhead |
|---|---|---|---|---|---|---|---|
| 1 | 25 | L | 5 | 5 | 5 | 5 | 4 |
|   | 12.5 | N | 5 | 5 | 5 | 5 | 3 |
| 2 | 25 | L | 5 | 4 | 5 | 5 | 3 |
|   | 12.5 | N | 5 | 3 | 5 | 4 | 2 |
| 3 | 25 | L | 5 | 5 | 5 | 5 | 3 |
|   | 12.5 | N | 5 | 4 | 5 | 4 | 3 |
| 4 | 25 | L | 5 | 5 | 5 | 5 | 3 |
|   | 12.5 | N | 5 | 4 | 5 | 4 | 2 |
| 5 | 25 | L | 5 | 4 | 5 | 5 | 5 |
|   | 12.5 | N | 5 | 4 | 5 | 5 | 4 |
| 6 | 25 | L | 5 | 5 | 5 | 5 | 4 |
|   | 12.5 | N | 5 | 4 | 5 | 5 | 3 |
| Chlomethoxynil | 25 | L | 5 | 5 | 5 | 4 | 3 |
|   | 12.5 | N | 5 | 4 | 5 | 3 | 2 |
| NIP | 20 | M | 5 | 4 | 4 | 3 | 1 |

TEST EXAMPLE 2

A 1/10,000-are pot was filled with soil to simulate a paddy field and grown with a weed such as barnyard grass, monochoria, umbrella plant, hotarui, or Arrowhead to an early stage of growth and treated with the chemical under test (the emulsifiable concentrate of Example 6 extended with water). Thereafter, each pot was treated in the same manner as in Example 1. The results obtained were as shown below.

TABLE 2

| Compound No. | Dosage of active ingredient (g/are) | Barnyard grass | Monochoria | Umbrella plant | Hotarui | Arrowhead |
|---|---|---|---|---|---|---|
| 1 | 25 | 5 | 5 | 5 | 5 | 5 |
|   | 12.5 | 5 | 5 | 5 | 5 | 5 |
|   | 6.25 | 5 | 5 | 5 | 5 | 4 |
| 3 | 25 | 5 | 5 | 5 | 5 | 5 |
|   | 12.5 | 5 | 5 | 5 | 5 | 4 |
|   | 6.25 | 5 | 5 | 5 | 4 | 4 |
| 5 | 25 | 5 | 5 | 5 | 5 | 5 |
|   | 12.5 | 5 | 5 | 5 | 5 | 5 |
|   | 6.25 | 5 | 5 | 5 | 5 | 5 |
| Chlomethoxynil | 25 | 5 | 5 | 5 | 5 | 5 |
|   | 12.5 | 5 | 5 | 5 | 5 | 3 |
|   | 6.25 | 5 | 5 | 5 | 4 | 2 |

TEST EXAMPLE 3

A polyethylene vat, 10 cm × 20 cm × 5 cm (depth), was filled with soil and seeded in drills with rice, barnyard grass, large crabgrass, or redroot pigweed and covered with soil to a thickness of 1 cm. Prior to the emergence, a prescribed quantity of the chemical under test (an aqueous composition of the emulsifiable concentrate of Example 6 extended with water) was uniformly sprayed over the soil in each pot. Twenty-one days after the treatment, the percent growth control was estimated by reference to untreated plot. The results obtained were as shown in Table 3.

TABLE 3

| Compound No. | Dosage of active ingredient (g/are) | Rice | Barnyard grass | Large crabgrass | Redroot pigweed |
|---|---|---|---|---|---|
| 1 | 25 | L | 5 | 5 | 5 |
|   | 12.5 | N | 5 | 5 | 5 |
| 3 | 25 | L | 5 | 5 | 5 |
|   | 12.5 | L | 4 | 5 | 5 |
| 5 | 25 | L | 5 | 5 | 5 |
|   | 12.5 | N | 4 | 5 | 5 |
| NIP | 25 | L | 5 | 5 | 4 |
|   | 12.5 | L | 3 | 5 | 3 |

What is claimed is:

1. A diphenyl ether represented by the general formula (I),

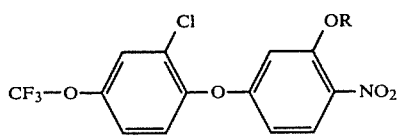

(I)

wherein R is a lower alkyl group having 1 to 4 carbon atoms, a lower alkoxyethyl group, the alkoxy substituent of which having 1 to 4 carbon atoms, or a lower alkoxyethoxyethyl group, the alkoxy substituent of which having 1 to 4 carbon atoms.

2. 3-Methoxy-4-nitro-2'-chloro-4'-trifluoromethoxy(diphenyl ether).

3. 3-Methoxyethoxyethoxy-4-nitro-2'-chloro-4'-trifluoromethoxy(diphenyl ether).

4. 3-Methoxyethoxy-4-nitro-2'-chloro-4'-trifluoromethoxy(diphenyl ether).

5. 3-Ethoxy-4-nitro-2'-chloro-4'-trifluoromethoxy(diphenyl ether).

6. 3-Ethoxyethoxy-4-nitro-2'-chloro-4'-trifluoromethoxy(diphenyl ether).

7. 3-Ethoxyethoxyethoxy-4-nitro-2'-chloro-4'-trifluoromethoxy(diphenyl ether).

8. 2,4-Bis(2-chloro-4-trifluoromethoxyphenoxy)nitrobenzene.

9. A compound of the formula:

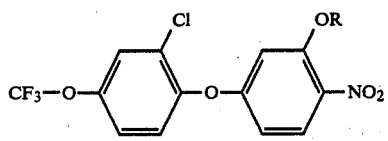

wherein R is methyl or ethyl.

10. A diphenyl ether according to claim 1 wherein R is a lower alkoxyethyl group or a lower alkoxyethoxyethyl group.

11. A process for producing a diphenyl ether represented by the general formula (I),

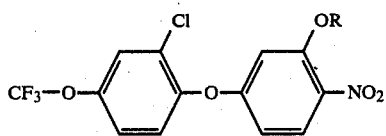
(I)

wherein R is a lower alkyl group having 1 to 4 carbon atoms, a lower alkoxyethyl group, the alkoxy substituent of which having 1 to 4 carbon atoms, or a lower alkoxyethoxyethyl group, the alkoxy substituent of which having 1 to 4 carbon atoms, which comprises reacting a compound having the formula,

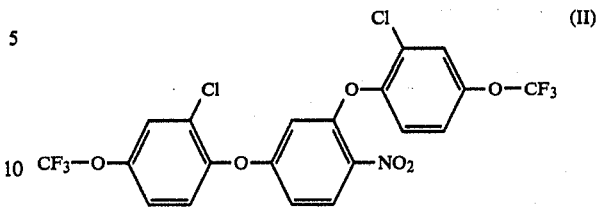
(II)

with a compound having the formula,

R—O—M     (III)

wherein R is the same as defined above and M is an alcoholate-forming metal atom.

12. The process of claim 11 wherein the temperature is 20° to 120° C.

13. A herbicide comprising as active ingredient a diphenyl ether represented by the general formula (I),

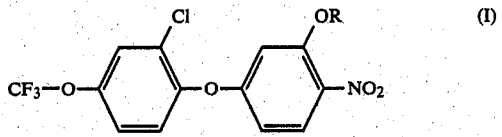
(I)

wherein R is a lower alkyl group having 1 to 4 carbon atoms, a lower alkoxyethyl group, the alkoxy substituent of which having 1 to 4 carbon atoms, or a lower alkoxyethoxyethyl group, the alkoxy substituent of which having 1 to 4 carbon atoms, and a diluent.

14. A herbicide comprising as active ingredient a diphenyl ether represented by the general formula:

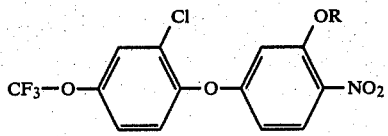

wherein R is methyl or ethyl, and a diluent.

* * * * *